US006214566B1

(12) United States Patent
Asa et al.

(10) Patent No.: US 6,214,566 B1
(45) Date of Patent: Apr. 10, 2001

(54) METHOD FOR DETECTING ANTI-SQUALENE ANTIBODIES

(75) Inventors: Pamela B. Asa, Memphis, TN (US); Robert F. Garry, New Orleans, LA (US)

(73) Assignee: The Administrators of the Tulane Educational Fund, New Orleans, LA (US)

( * ) Notice: Subject to any disclaimer, the term of this patent is extended or adjusted under 35 U.S.C. 154(b) by 0 days.

(21) Appl. No.: 09/193,115

(22) Filed: Nov. 16, 1998

(51) Int. Cl.[7] .............................. G01N 33/53; C12Q 1/06; C07K 16/00
(52) U.S. Cl. ......................... 435/7.1; 435/39; 530/387.1
(58) Field of Search .................... 435/7.1, 39; 530/387.1

(56) References Cited

PUBLICATIONS

Rodriguez, Paul M., "Sickness and Secrecy," Insight, pp. 7–13 (Aug. 25, 1997).
Speech by Dr. Bernard Rostker, Special Assistant to the Deputy Secretary of Defense for Gulf War Illnesses Before the Worldwide Chemical Conference, Fort McClellan, Alabama (Jun. 25, 1998) http://www.gulflink.osd.mil/chemspch 062598.html).

Fukuda et al., "Chronic Multisymptom Illness Affecting Air Force Veterans of the Gulf War," *JAMA* 280:981–988 (1998).

Jennings, Veronica M., "Review of Selected Adjuvants Used in Antibody Production," *ILAR Journal 37* :119–125 (1995).

Ray Colliton, "Link to Innoculations Found in Some GWS Vets," (Sep. 1997) http://www.sonic.net/daltons/melissa/gws5.html.

*Primary Examiner*—Hankyel T. Park
(74) *Attorney, Agent, or Firm*—Howrey Simon Arnold & White, LLP

(57) ABSTRACT

Gulf War Syndrome is an ill-defined disease affecting thousands of individuals. A correlation is believed to exist between Gulf War Syndrome and the presence of antisqualene antibodies in affected individuals. The invention discloses a method and a kit useful for identifying the presence or absence of antisqualene antibodies. A diagnosis of Gulf War Syndrome is suggested for individuals having detectable levels of antisqualene antibodies.

12 Claims, No Drawings

METHOD FOR DETECTING ANTI-SQUALENE ANTIBODIES

FIELD OF THE INVENTION

The invention relates to methods and immunoassay kits that are useful to aid in the diagnosis of Gulf War Syndrome (GWS). A correlation between the presence of antisqualene antibodies and incidence of GWS has been discovered. Development of methods for the detection of antisqualene antibodies in a test sample facilitates the diagnosis of GWS.

BACKGROUND OF THE INVENTION

The illnesses afflicting men and women who served in the Persian Gulf military conflict during 1990–1991 remain ill-defined. A constellation of symptoms including fatigue, rashes, headaches, arthralgias, myalgias, diarrhea, memory loss, autoimmune thyroid disease, increased allergies and sensitivities to environmental elements, and neurological abnormalities collectively referred to as Gulf War Syndrome (GWS) have been described (Grady, et al. *Arch. Int. Med.* 158: 367–371, 1998; Persian Gulf Veterans Coordinating Board. *Arch. Int. Med.* 155: 262–268, 1995; Haley, et al. *J.A.M.A.* 277: 231–237, 1997). While GWS patients do not in general suffer from classic rheumatic diseases, the signs and symptoms are reminiscent of atypical connective tissue diseases such as fibromyalgia, chronic fatigue syndrome, and the process associated with exposure to silicone breast implants (SBI). Serological abnormalities including hypergammaglobulinemia and abnormal serum proteins have been reported in 45% of GWS patients (Grady, et al. *Arch. Int. Med.* 158: 367–371, 1998).

Hundreds of explanations for GWS have been proposed. In 1994, the U.S. Secretary of Defense and the Secretary of Veterans Affairs asked the Center for Disease Control and Prevention to conduct an official scientific study exploring possible causes of GWS. The study was aimed at organizing reported symptoms into a defined case, characterizing clinical features, and evaluating risk factors. The results are described by Fukuda, et al (*J.A.M.A.* 280: 981–988, 1998). Fukuda et al, assessed a population of Gulf War Veterans with respect to many of the proposed explanations for GWS. The study included assessment of physical symptoms; blood, urine, and stool analysis; and serological assays. Tests were conducted to detect the presence of various viruses, bacteria, mycoplasm, and parasites. Serum was tested for yellow fever, dengue, Sindbis, West Nole, and phlebotomus fever viruses (Naples and Sicilian); Toscana, Karimbad, and Isfahan viruses; *Rickettsia typhi* and *Rickettsia rickettsii; Coxiellla burnetii; Ehrlichia chaffeensis; Leishmania tropica* and *Leishmania donovani; Toxoplasma gondii; Schistosoma mansoni* and *Schistosoma haematobium; Strongyloides stercoralis; Helibacter pylori; Clostridium botulinum;* and *Bacillus anthracis.* Stool specimens were tested for red and white blood cells; ova and parasites of *Cryptosporidium parvum, Cyclospora cayetanensis, Isospora belli,* and microsporidia; enteroviruses; and bacteria strains of Salmonella, Shigella, Yersinia, Campylobacter, and *Escherichia coli* (0157:H7). While this study is considered an official and comprehensive report on GWS, no attempt was made to assess alternative explanations, such as adjuvant's disease.

Other theories, implicating exposure to chemical and biological agents as a cause of GWS, have been the subject of numerous studies. These studies, however, neither conclusively identify a causative agent for the disease nor properly explain the pathology observed in GWS cases.

The Persian Gulf Veterans Coordinating Board has addressed the possibility of exposures to chemical and biological agents. The Board, however, attempted to account for these illnesses without defining a molecular pathology (Persian Gulf Veterans Coordinating Board. *Arch. Int. Med.* 155: 262–268, 1995).

Haley grouped reported symptoms into seven different syndromes based upon possible exposure to various chemicals present at the time of the Persian Gulf Conflict (Haley, et al. *J.A.M.A.* 277: 231–237, 1997). While this study does attempt to categorize possible causes of the disease, it fails to explain the GWS pathology observed in the veterans. Furthermore, the study did not outline the pathology one would expect to observe in those exposed to the various chemical agents.

Abou-Donia examined acute toxicity of pyridostygmine bromide and organophosphates in chickens (Abou-Donia, et al. *J. Tox. Environ. Health.* 48: 35–56, 1996). The study compared chickens suffering from acute toxicity to the condition presented by GWS patients. However, since many Gulf War veterans did not develop GWS until months or years after the military conflict, an animal model which employs a rapid acute response to mimic the symptoms of GWS may not be appropriate. As a result, the study examining acute toxicity in chickens may not be relevant to a human disease characterized by a delayed onset. Furthermore, the study did not fully reflect the molecular pathology observed in actual GWS cases.

While chemical toxicity may mimic some of the GWS symptoms, it cannot account for all of them. For instance, exposure to organophosphates has never been associated with the development of immunological abnormalities (Vial, et al. *J. Tox. Environ. Health.* 48: 215–229, 1996). Chronic organophosphate pesticide intoxication in two mammalian species neither interfered with cell-mediated immunity, nor induced autoimmunity (Jha, et al. *Acta. Vet. Hung* 38: 55–60, 1990). Clearly, this is distinct from GWS, which displays a multitude of symptoms linked to immune dysfunction.

An additional example involving chemical agents is provided by the large numbers of individuals exposed to sarin in the Japanese subway Mar. 20, 1995. Acetylcholinesterase levels were monitored and observed to return to normal levels in all patients by three months following exposure. Some subclinical miosis and neuropathy were present 30 days after exposure, but these disappeared after a year (Morita, et al. *Lancet.* 346: 290–3, 1995). Tissue distribution of sarin and its metabolites, as well as the time course of detoxification following exposure is known (Little, et al. *Toxicol. Appl. Pharmacol.* 83: 412–419, 1986). The physiological effects are immediate and the pathology is well documented. In no case has there been reports of any delayed onset of autoimmune disorders.

No exposures to chemical agents which required medical treatment were documented by U. S. military personnel. Such exposures typically require the use of ventilatory or circulatory supports, or atropine and anticonvulsants to combat the onset of acute symptoms. Low dose effects were also not observed (Dr. Bernard Rostker, Pentagon, personal communication; Col. Edward Koenigsburg, USAF, Persian Gulf Investigation, Falls Church, Va., personal communication). Such effects have been studied in primates and generally abate within 24 hours of the exposure (Wolthuis, et al. *Pharmacol. Biochem. Behav.* 51: 443–456, 1995).

Others have proposed that GWS is a type of post-traumatic stress syndrome (Hyams, et al. *Ann. Int. Med.* 125:

398–405, 1996). It is difficult, however, to reconcile this hypothesis with the symptoms manifest in afflicted individuals.

An additional explanation has been outlined in which GWS results from a dysregulation of the immune system. (Hyams, et al. *Ann. Int. Med.* 125: 398–405, 1996). The GWS patients suffer from various symptoms similar to those having autoimmune diseases, but cannot be diagnosed with a "classic" rheumatic disease. Gulf War veterans and attendant civilian personnel received a variety of immunizations in preparation for possible deployment to the Persian Gulf theater (David, et al. *Br. Med. J* 314: 239–240, 1997). It has been suggested that GWS may result from an imbalance in the immune system. It was hypothesized that the imbalance may be due to an adverse reaction to a vaccination.

It was noted in some patients that the onset of illness occurred within weeks of receiving a full complement of immunizations. These individuals displayed symptoms of GWS soon after vaccination and were not deployed. Other individuals were deployed, but returned home before the start of the war because of severe joint and muscle pain, as well as neurological problems. Additional personnel from the Gulf War became ill years later. These individuals, however, report the same symptoms as those who became ill only weeks after their vaccinations. The variability in the onset of disease symptoms, as well as differences in their severity, may be due to individual immune responses. Such variability is reportedly regulated at a genetic level involving the histocompatibility complex (Madzhidov, et al. *Biull. Eksp. Biol. Med.* 102: 74–76, 1986; Lorentzen, et al. *Transplant. Proc.* 27:1532–1534, 1995).

A possibility exists that the immunizations administered to all personnel involved in the Gulf War may be linked to the etiology of GWS. The immunizations administered typically comprised an antigen and an immunological adjuvant. The adjuvants function to boost the protective effect of the immunization by eliciting a stronger immune response against the antigen. The adjuvants are capable of stimulating the immune system's cell-mediated and humoral responses against the antigen being administered. Cases have been reported, however, where the adjuvants cause a more generalized and indiscriminate stimulation of the immune system. This can disrupt the balance of self-regulatory mechanisms within the immune system and lead to autoimmune disease (Kleinau, et al. *Scand. J. Rheumatol.* 101: 179–181, 1995; Madzhidov, et al. *Biull. Eksp.*

Biol. Med. 102: 74–76, 1986; Lorentzen, et al. *Transplant. Proc.* 27: 1532–1534, 1995).

The adjuvant most commonly used is alum, which is most often provided as aluminum hydroxide, $Al(OH)_3$. This adjuvant appears to induce its effect by slowing the release of antigen from an antigen/adjuvant complex, as well as by other immunostimulatory properties such as attraction of immunocompetent cells to the injection site. In preparing vaccines, antigens are physically precipitated with hydrated insoluble salts of aluminum hydroxide or aluminum phosphate. The resulting composition is further processed and provided in a convenient form for administration. Alum is the only adjuvant approved by the Food and Drug Administration (FDA) for human use. It has been given to millions of people world-wide in various vaccines with no reports of significant problems (Warren, H. S., et al. *Ann. Rev. Immunol.* 4:369–388, 1986).

Although not approved by the FDA for use in humans, squalene has been used as an adjuvant in experimental vaccines against a variety of pathogens including *Bacillus anthracis* (Ivans, et al. *Vaccine.* 13: 1779–1783, 1995), *Plasmodium falciparum,* (Hoffman, et al. *Am. J Trop. Med. Hyg.* 51: 603–612, 1994), and herpes simplex virus (Burke, et al. *J. Inf. Dis.* 170: 1110–1119, 1994). The effectiveness of adjuvants has been shown to correlate with toxicity. This toxicity typically manifests with the onset of autoimmune disease symptoms (Koga, et al. *Microbiol. Immunol.* 30:717–723, 1986; Zamma, et al. *Infect. Immun.* 39: 1291–1299, 1983).

A study using squalene as an adjuvant in an influenza vaccine reported moderate to severe local and systemic immune reactions in humans (Keutek, et al. *Vaccine.* 11: 909–913, 1993). The participants reported induration, erythema, lymphadenopathy, fever, chills, nausea, and dizziness lasting for several days.

Another squalene-containing vaccine was used with gp120 in a candidate human immunodeficiency virus (HIV) vaccine. In this case, induction of severe systemic and local reactions was reported in 15 of the 30 participants (Keefer, et al. *AIDS Res. Hum. Retro.* 12: 683–693, 1996). Similarly, in a study of a simian immunodeficiency (SIV) vaccine in macaques, squalene was used as an adjuvant. The animals in this study developed anti-human-cell antibodies and various other autoimmune-like symptoms (Vaslin, et al. *Int. Conf. AIDS* 8(2):A42, 1992).

Several adjuvants have reportedly produced autoimmune diseases in experimental models. Adjuvant-induced arthritis is a well-characterized autoimmune disease which can be induced in rats and other species (Kleinau, et al. *Scand. J. Rheumatol.* 101: 179–181, 1995; Madzhidov, et al. *Biull. Eksp. Biol. Med.* 102: 74–76, 1986; Lorentzen, et al. *Transplant. Proc.* 27: 1532–1534, 1995). The disease process in these cases is complex, often affecting multiple organ systems. For example, cachectic syndrome (Rofe, et al. *Agents Actions.* 42: 60–62, 1994) and testicular dysfunction (Clemons, et al. *J. Androl.* 10: 419–424, 1989) have been associated with adjuvant-induced arthritis. Uveitis, a T-cell mediated intraocular inflammatory disease, can also be induced by adjuvants (Petty, et al. *J. Rheumatol.* 16: 400–405, 1989). Additional reports have shown that various neurological disorders, commonly manifest in patients with autoimmune diseases, may be the result of immunological dysfunction (Rogers, et al. *Molecular Med. Today.* 2: 76–81, 1996; Tekin, et al. *Dementia* 7: 91–94, 1996; Honnorat, et al. *Arch. Neurol.* 52: 462–468, 1995; Wucherpfennig, et al. *Res. Publ. Assoc. Res. Nerv. Ment. Dis.* 68: 105–116, 1990; Cross, et al. *Am. J. Pathol.* 139: 1401–1409, 1991; Bansal, et al. *J. Clin. Pathol.* 47: 300–302, 1994; McNicholl, et al. *J. Rheumatol.* 21: 1061–1066, 1994; Zanone, et al *Diabetologia.* 36: 564–569, 1993; Moll, et al. *Neurology.* 43: 2574–2581, 1993).

GWS may also be a form of "adjuvants disease." It has been hypothesized that GWS may be caused by squalene administered in a vaccine to many Gulf War personnel. This theory, however, has been discounted by government and military officials. A report, prepared by the U.S. Army Medical Research and Material Command in 1996, discusses the squalene theory. "The basic hypothesis and supporting evidence presented are flawed or inaccurate. . . . Available information strongly argues against [this] hypothesis." The report goes on to outline seven reasons why the squalene theory is implausible or wrong (Rodriquez, "Sickness and Secrecy," *Insight on the News.* Aug. 25, 1997, pg. 9–10).

In addition to this rejection by the military and government, the squalene theory has been largely ignored by the scientific community. As discussed above, nearly all of the scientific studies investigating the causes of GWS have focused on chemical and biological agents (e.g. Fukuda, et al. *J.A.M.A.* 280: 981–988, 1998; Haley, et al. J.A.M.A. 277: 231–237, 1997; Persian Gulf Veterans Coordinating Board. Arch. Int. Med. 155: 262–268, 1995; Abou-Donia, et al. *J. Tox. Environ. Health.* 48: 35–56, 1996; Hyams, et al. *Ann. Int. Med.* 125: 398–405, 1996). These scientific studies have not adequately addressed the role of squalene in the etiology of GWS. Yet many close parallels exist between the symptoms of GWS and those observed in "adjuvants disease." Clearly, rejection of the squalene theory is premature. Thus, despite its dismissal by many scientific, governmental, and military organizations, the squalene theory is not adequately understood and warrants further study. More information is needed to discern the role that this adjuvant may play in the onset of GWS symptoms.

Understanding GWS at a molecular level is a first step towards identifying its cause and providing a successful treatment. To make this possible, diagnosis of patients with GWS needs to be more reliable. Reliable diagnosis is currently difficult given the wide array of symptoms associated with the disease. Thus, there exists a need in the art for new methods to aid in the diagnosis of GWS.

DEFINITIONS

The following definitions are provided in order to aid those skilled in the art in understanding the detailed description of the present invention.

"Antigenic epitope" refers to any discrete segment of a molecule, protein, or nucleic acid capable of eliciting an immune response, wherein the immune response results in the production of antibodies reactive with the antigenic epitope.

"Antisqualene antibody" refers to an antibody capable of complexing with squalene. Such an antibody may complex with squalene, or with any antigenic epitope presented by squalene.

"ASA" refers to antisqualene antibody.

"Binary complex" refers to a complex comprising squalene and an antisqualene antibody.

"Detectable label" refers to molecule, protein, or nucleic acid which may be detected either directly or indirectly through the use of a suitable detection agent or detection device.

"Detection agent" refers to a composition providing conditions suitable for detecting a detectable label. Such compositions often allow the observation of a calorimetric, fluorescent, or chemiluminescent signal when the detectable label is contacted with the detection agent.

"GWS" refers to Gulf War Syndrome.

"Indicator reagent" refers to a molecule, protein, or nucleic acid capable of complexing with an antisqualene antibody. The binding component is conjugated to a detectable label.

"Squalene" refers to a hydrocarbon of the chemical formula $C_{30}H_{50}$, 2,6,10,15,19,23-hexamethyl-2,6,10,14,18,22-tetracosahexaene, CAS Number [111-02-4].

"Ternary complex" refers to a complex comprising squalene, an antisqualene antibody, and an indicator reagent.

SUMMARY OF THE INVENTION

In a preferred embodiment, the present invention is directed towards an immunoassay for detecting antisqualene antibodies. In an additional inventive embodiment, a kit is provided to facilitate performance of the immunoassay. The method of the immunoassay typically comprises several steps, as outlined below.

Formation of a Binary Complex

A test sample suspected of containing antisqualene antibodies is provided. The sample is contacted with squalene. This may result in the formation of a binary complex comprising the squalene and any antisqualene antibodies contained in the test sample. The binary complex may be washed several times to effectively remove any uncomplexed material.

Formation of a Labeled Ternary Complex

The binary complex may then be contacted with an indicator reagent. The indicator reagent typically comprises a binding molecule capable of complexing with an antisqualene antibody. This may result in the formation of a ternary complex comprising squalene, antisqualene antibody, and the indicator reagent. The indicator reagent is generally conjugated to a detectable label. This ternary complex may be washed several times to remove any uncomplexed material.

Formation of a Labeled Ternary Complex in a Single Step

Alternatively, the test sample may be contacted with squalene and the indicator reagent in a single simultaneous step. A ternary complex may form. A complex formed in this manner may be washed and detected as described in the preferred embodiment.

Detection and Diagnosis

The ternary complexes may then be detected either directly, or with a suitable detection agent. The particular detection agent selected will depend on the type of detectable label used. A positive signal indicates the presence of antisqualene antibodies in the test sample. This may be indicative of a diagnosis of Gulf War Syndrome in an individual providing the test sample. Conversely, the absence of a signal may indicate the absence of antisqualene antibodies in the individual providing the test sample.

The test sample may generally be any type of biological material containing antibodies. Such materials may be processed so that they are provided in a suitable form. The test sample is preferably provided from a bodily fluid, more preferably is provided from blood, and most preferably provided from serum.

The organism providing the test sample may generally be any organism which contains antibodies. The organism preferably is a mammal, and more preferably is a human.

The squalene provided in the above method may be immobilized on a solid support. The solid support may be provided in one of many different forms. These forms may include a membrane, filter, plastic, bead, agarose bead, SEPHAROSE (SEPHAROSE is a registered trademark of Pharmacia Biotech, Piscataway, N.J.) bead, or magnetic bead.

In addition to the different forms, the solid support may be made from a variety of materials. The solid support is preferably nitrocellulose, polyvinylidene difluoride, nylon, rayon, cellulose acetate, agarose, SEPHAROSE, metal, polypropylene, polyethylene, polystyrene, polyvinyl chloride, polyvinyl acetate, polyamide, polyimide, polycarbonate, polyether, polyester, polysulfone, polyacetal, or polymethyl methacrylate, more preferably is polypropylene, polystyrene, polyvinylchloride, polyamide, polycarbonate, polyether, polymethyl methacrylate, nitrocellulose, polyvinylidene difluoride, or nylon, and most preferably is nitrocellulose.

The squalene may generally be from any source. Commercial preparations are readily available (Sigma, St. Louis, Mo.). Alternatively, it may be synthesized from various precursors or obtained from an organism. Squalene is a relatively large hydrocarbon which may contain multiple antigenic epitopes. As a result, any portion of squalene containing an antigenic epitope may be used in place of squalene in the present invention. In addition, other molecules having antigenic epitopes in common with those of squalene may be used in an equivalent fashion. Such equivalent molecules may include oxidosqualene, squalene precursors such as farnesyl bromide and trans-geranylacetone, as well as other intermediates formed in the sterol biosynthetic pathway.

The indicator reagent is typically conjugated to a detectable label. The detectable label may be an enzyme, such as alkaline phosphatase, β-galactosidase, or peroxidase; a protein, such as biotin or digoxin; a fluorochrome, such as rhodamine, phycoerythrin, or fluourescein; a fluorescent protein, such as GFP or one of its many modified forms; a radioisotope; or a nucleic acid segment.

Some of these detectable labels can be detected directly. Fluorochromes (Wells and Johnson. In *Three-Dimensional Confocal Microscopy*, pp. 101–129, 1994) and fluorescent proteins (Sakai, et al. *J. Cell Biol.* 139(6): 1465–1476, 1997) may be directly detected with a suitable detection device, such as a fluorescent microscope, fluorescent activated cell sorter (FACS), or fluorometer. Radioisotopes may be detected through the use of a scintillation counter or Geiger counter.

Other labels may be detected indirectly. These labels may require the use of a suitable detection agent. The choice of a suitable detection agent generally depends on which detectable label is used.

For example, if a protein such as biotin is used as the detectable label, a detection agent comprising avidin or streptavidin is generally employed (Bayer, et al *Meth Biochem Anal* 26: 1–10, 1980). In such cases, a suitable detection agent generally comprises a binding component capable of complexing with the protein. This binding component may be further detected by contacting it with a second detectable label.

Enzymes, such as horseradish peroxidase, alkaline phosphatase, and β-galactosidase, may also be used as detectable labels. Detection agents for enzymes generally utilize a form of the enzyme's substrate. The substrate is typically modified, or provided under a set of conditions, such that a chemiluminescent, colorimetric, or fluorescent signal is observed after the enzyme and substrate have been contacted (Vargas, et al. *Anal Biochem* 209: 323, 1993).

Nucleic acids, when used as detectable labels, may be detected by using a hybridizing probe. This probe may be conjugated to an additional detectable label which, when placed under suitable conditions, provides a fluorescent, chemiluminescent, colorimetric, or radioactive signal. Alternatively, the nucleic acid may be amplified by means of a polymerase chain reaction (Dirks, et al. *J Histochem Cytochem* 38, 467–476, 1990). Once amplified, the nucleic acid may be easily detected by gel electrophoresis.

Radioisotopes, in addition to the direct method mentioned above, may be detected indirectly by autoradiography (e.g. exposure to film).

There are many other suitable detection methods compatible with the instant invention. In each case, the detection agent and its method of use are well known to one of ordinary skill in the art.

A diagnostic kit may be designed to aid the performance of the above method. Such a kit may contain vessels containing squalene and the indicator reagent, respectively. The kit may further contain various blocking buffers, buffers to aid the formation of binary and ternary complexes, wash buffers, and detection agents. One of ordinary skill in the art is aware that these buffers may vary in their composition, but still be compatible with the present invention. All such variations are considered equivalent for the purposes of present invention.

The squalene in the diagnostic kit, as previously mentioned, may be provided in many structurally equivalent forms. In addition, the squalene may be provided from any source, natural or synthetic.

The squalene in the diagnostic kit may be provided already immobilized on a solid support. This solid support may be provided in one of many different forms. These forms may include a membrane, filter, plastic, agarose bead, SEPHAROSE bead, or magnetic bead.

In addition to the different forms, the solid support may be made from a variety of materials. The solid support is preferably nitrocellulose, polyvinylidene difluoride, nylon, rayon, cellulose acetate, agarose, SEPHAROSE, metal, polypropylene, polyethylene, polystyrene, polyvinyl chloride, polyvinyl acetate, polyamide, polyimide, polycarbonate, polyether, polyester, polysulfone, polyacetal, or polymethyl methacrylate, more preferably is polypropylene, polystyrene, polyvinylchloride, polyamide, polycarbonate, polyether, polymethyl methacrylate, nitrocellulose, polyvinylidene difluoride, or nylon, and most preferably is nitrocellulose.

The diagnostic kit may further comprise a detection agent. As previously mentioned, the choice of a suitable detection agent generally depends on which detectable label is used. Many different detectable labels and detection agents are compatible with the present invention.

The components of the diagnostic kit may be provided in many different forms and quantities. Various types of packaging are also possible. Any such alternative embodiments are considered equivalent to the present invention.

The following examples are included to demonstrate preferred embodiments of the invention. It should be appreciated by those of skill in the art that the disclosed examples represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLES

A group of GWS patients who served in the United States military during Desert 5 Shield/Desert Storm or worked as civilian employees to the U.S. military or their contractors in the Persian Gulf during 1990–1991 was identified. This group served in all branches of the military and received a full complement of immunizations. The group served in various locations in the Persian Gulf, including on board U.S. Navy vessels which were not in combat or exposed to environmental toxins. These individuals reported similar disease symptoms which are multisystemic in nature. Antibodies reactive with squalene, an experimental immunological adjuvant, were found in a high percentage of these GWS cases.

Example 1
Selection of Participants for the Study

Participants were admitted to the study based upon their service in the United States military, as a civilian employee of the U.S. military, or as an employee of a military contractor in the Persian Gulf during 1990–1991. Individuals showing no symptoms of GWS, as well as those displaying overt signs of the disease were tested. In addition, individuals who had been immunized prior to duty in the Persian Gulf, but were not deployed were tested. None of these individuals had received squalene in any previous experimental trials (although several individuals were tested who had previously received squalene). Additional control populations included patients with atypical autoimmune disease (associated with the implantation of silicone), patients with idiopathic autoimmune diseases, and healthy subjects.

Clinical records and histories were obtained for each of the participants in the study. Symptoms, diagnostic laboratory tests (where available), and general clinical information were obtained and recorded.

Example 2
Collection of Samples for Testing

Serum samples from study participants were collected, stored at -20° C., and sent to Tulane University School of Medicine in New Orleans. Samples from the Gulf War era participants were provided in a blinded manner. The identities and exact number of samples from each category were not made available to Tulane researchers until after completion of the diagnostic testing portion of the study. All samples were tested twice under the same conditions. Results were consistent in both tests for all of the samples.

Example 3
Preparation of squalene on a solid support

The anti-squalene antibody (ASA) assay measures the specific binding of serum immunoglobulin (IgG) to squalene immobilized on a solid support. To accomplish this, squalene (>98% purity, Sigma, St. Louis, MO) was diluted 10, 100, 1000, and 10,000 fold in distilled water, applied to nitrocellulose membranes, (Schleicher and Schueil, Keene, N.H.) and allowed to air dry. The nitrocellulose membranes were then cut into 4 is mm wide strips, placed in 20-well plates, and rinsed with a wash buffer (Tris-buffered saline containing 0.3% (v/v) polyoxy-ethylene sorbitan monolaurate and 0.005% (w/v) Thimerosal; pH 7.4). The strips were incubated in 2 ml blocking buffer (Tris-buffered saline containing 5% (w/v) powdered instant milk, 4% (v/v) goat serum and 0.008% (w/v) Thimerosal; pH 7.4) for 45 minutes.

Example 4
Formation of a binary complex

Blood samples were collected by venipuncture into red top tubes and allowed to clot overnight at 4° C. Serum was then collected from each of the tubes with a capillary pipette. The sera (5 $\mu$l) were added to the membrane strips and blocking buffer at a final dilution of 1:400. The sera was allowed to incubate for 90 minutes. All incubations and washes were carried out at room temperature on a rocking platform. The blocking buffer (containing the test sera) was then removed, and the strips were washed (3 changes of wash buffer over 15 minutes).

Example 5
Formation of a Ternary Complex

After washing, 2 ml of blocking buffer containing an indicator reagent were added. In this example, the indicator reagent was solution containing goat anti-human IgG antibody conjugated to biotin (1 mg/mL, Kirkengaard & Perry Laboratories; Gaithersburg, MD). The indicator reagent was used at a dilution of 1:1000. After a 60 minute incubation, the strips were again washed (3 changes of wash buffer over 15 minutes). A solution of avidin conjugated to horseradish peroxidase was then added (1 mg/mL, Jackson ImmunoResearch Laboratories, Inc.; West Grove, Pa.). The avidin was added to a final dilution of 1:500. Following another 60 minute incubation, the strips were washed again (3 changes of wash buffer over 15 minutes).

Example 6
Detection of a Ternary Complex

After washing, 2 ml of detection buffer (phosphate buffered saline containing 30% (v/v) methanol, 0.6 mg/ml 4-chloro-1-napthol, 0.03% (v/v) hydrogen peroxide; pH 7.4) were added. This results in a reaction generating a color change on the strip. The intensity of this color depends on the number of labeled ternary complexes present on the strip. The reaction was allowed to proceed for 15 minutes, and was stopped by rinsing the strips in distilled water. The strips were allowed to air dry. A relative scale of color intensity was established from 0 to 4+. A 4+ represents the highest reactivity, as manifested by the most intense color on the membrane. More intermediate reactivity displays variations which are less intense in color. These are represented by relative scores of 1+, 2+, and 3+ (from lower to higher intensities). A zero indicates an absence of reactivity as seen by a lack of color. Each sample was scored visually and assigned a value on this scale.

At the end of the study, results of the anti-squalene antibody (ASA) assay were compared with the clinical data of each participant. The strength of binary relationships was tested using chi square tests of independence. The tests demonstrated a statistically significant difference between the test populations and the control groups.

Example 7
Recording of Symptoms Reported by the Participants in the Study.

Some individuals deployed to the Persian Gulf received a full complement of immunizations and became sick with GWS (Table 1). These GWS patients display many signs and symptoms of autoimmune connective tissue and neurological disease with arthritis (94%), fibromyalgia (94%), lymphadenopathy (94%), rashes (94%), weakness (86%), fatigue (81%) chronic headaches (78%), and memory loss (72%) as the most frequent symptoms. Many of these GWS patients also had abnormal values for several lab tests, including positive antinuclear antibodies (17%), anti-dsDNA (14%), low C3 and C4 (14%), anemia (14%), anti-thyroid microsomal antibodies (14%), and elevated ESR and/or CRP (22%). A minority of symptomatic patients met diagnostic criteria for classical autoimmune disease, including Sjogren's syndrome (8%), multiple sclerosis (3%), ALS (8%), and systemic lupus erythematosus (14%). It should be noted, however, that most patients did not have an optimal work up for connective tissue and neurological autoimmune diseases because of limited resources in the Veterans' Administration Hospital or military hospitals.

Individuals who were vaccinated, but not deployed, displayed a similar array of signs and symptoms. Frequencies of arthritis (100%), fibromyalgia (100%), lymphadenopathy (100%), rashes (100%), weakness (100%), fatigue (100%), chronic headaches (100%), and memory loss (100%) were similar to those reported by the deployed individuals (Table 1). The non-deployed individuals in our study had a higher rate of dizziness (100%), seizures (33%), and neuropsychiatric abnormalities (83%) than the deployed group. These differences were not statistically significant, because the number in this group was small. Laboratory tests for the group of non-deployed individuals were also abnormal with positive antinuclear antibodies (33%), anemia (33%), and elevated ESR and/or CRP (50%).

In contrast, abnormal signs, symptoms and laboratory tests were rare in the group of Gulf War era veterans that considered themselves to be healthy. These individuals reported some signs and symptoms of GWS, but their illnesses were not multisystemic and occurred at a low frequency overall (Table 1). Those signs and symptoms reported included fibromyalgia (8%), chronic fatigue (33%), weakness (17%), memory loss (25%), and thyroid disease (8%).

TABLE 1

Signs, symptoms and laboratory tests results of Gulf War era subjects.

| Parameters | Deployed Sick (n = 38) | Deployed Well (n = 12) | Non-Deployed Sick (n = 6) |
|---|---|---|---|
| Arthritis | 94% | 0% | 100% |
| Fibromyalgia | 94% | 8% | 100% |
| Lymphadenpathy | 94% | 0% | 100% |
| Rashes | 94% | 0% | 100% |
| Photosensitive rashes | 25% | 0% | 67% |
| Malar rashes | 17% | 0% | 50% |
| Chronic fatigue | 81% | 33% | 100% |
| Chronic headaches | 78% | 0% | 100% |
| Abnormal hair loss | 19% | 0% | 33% |
| Skin lesions | 42% | 0% | 50% |
| Aphthous ulcers | 36% | 0% | 50% |
| Dizziness | 47% | 8% | 100% |
| Chronic diarrhea | 36% | 0% | 53% |
| Night sweats | 36% | 0% | 83% |
| Low grade fevers | 39% | 0% | 83% |
| Weakness | 86% | 17% | 100% |
| Memory loss | 72% | 25% | 100% |
| Seizures | 14% | 0% | 33% |
| Mood changes | 72% | 0% | 67% |
| Neuropsychiatric abnormalities | 44% | 0% | 83% |
| +FANA1 | 17% | 0% | 33% |
| Anti-dsDNA antibodies | 14% | 0% | ND2 |
| Low C3 and C4 | 14% | 0% | ND |
| Anti-thyroid microsomal antibodies | 14% | 0% | ND |
| Anemia | 14% | 0% | 33% |
| Elevated ESR &/or CRP | 22% | 0% | 50% |
| Autoimmune cardiopathy | 11% | 0% | 17% |
| Autoimmune thyroid disease | 17% | 0% | ND |
| Systemic lupus erythematosus | 14% | 0% | 33% |
| Multiple sclerosis | 3% | 0% | ND |
| Amyotrophic lateral sclerosis | 8% | 0% | 0% |
| Reynaud's Phenomena | 42% | 0% | 67% |
| Sjögren's syndrome | 8% | 0% | ND |

1 Fluorescent antinuclear antibodies
2 Not determined

Example 8

Quantifying ASA Levels.

In order to determine why military personnel, initially found fit for duty during war, developed symptoms common to autoimmune diseases, blood samples were collected from several groups of veterans. Many studies have shown that adjuvants used to enhance vaccine efficacy can induce autoimmune diseases. Therefore, we wished to determine if GWS patients, who received immunizations from the military, had antibodies reactive with the adjuvant squalene.

An anti-squalene antibody assay was performed as described in Examples 2–6. The results are shown in Table 2.

TABLE 2

ASA Reactivity in Gulf War Vets and Healthy Blood Donors

| Sample No. | ASA Score | Sample No. | ASA Score | Sample No. | ASA Score |
|---|---|---|---|---|---|
| 1 | 4+ | 8 | 1+ | 15 | 0 |
| 2 | 3+ | 9 | 1+ | 16 | 0 |
| 3 | 2+ | 10 | 1+ | 17 | 0 |
| 4 | 2+ | 11 | 0–1+ | 18 | 0 |
| 5 | 2+ | 12 | 0–1+ | 19 | 0–1+ |
| 6 | 1+ | 13 | 0–1+ | 20 | 1+ |
| 7 | 1+ | 14 | 0–1+ | | |

Note: Samples 1–16 are Gulf War Veterans; Samples 17–20 are healthy individuals.

After testing the serum samples, it was determined that GWS patients who were deployed had antisqualene antibody (ASA) responses ranging in intensity from 1+to 4+. Most of these individuals displayed a reactivity from 2+to 3+at a serum dilution of 1:400. One individual who had an especially strong reaction scored a 4+.

To further assess the correlation between GWS and the presence of ASA, samples were tested from the 56 individuals providing the clinical data in Table 1. The ASA assay revealed that a substantial majority of deployed individuals with GWS were positive for ASA (95%, n=38). Interestingly, sera from individuals with GWS who were not deployed also displayed reactivity to ASA (100%, n—6). In contrast, none of the Gulf War veterans who considered themselves healthy were positive for ASA (0%, n=12). All three groups, however, received a full complement of immunizations.

Example 9
Comparing ASA Levels in Gulf War Veterans with General Population.

In a broader antibody-screening study, antibodies to squalene were studied in larger groups of individuals. Blood samples of Gulf War veterans from different medical centers were tested for ASA. This group (n=86) contained a high percentage of ASA positive individuals (69%). The samples included in this group were not segregated according to their clinical status and therefore included healthy individuals. Because squalene is in some cosmetic products, it may be that ASA is present in a larger segment of the general population. Samples of blood from blood banks were tested, however, and indicated that only 5% (n=48) were positive for ASA. All of these positive tests displayed lower color intensities.

Example 10
Determining ASA Levels in Various Autoimmune Disorders

To determine if antibodies to squalene were present in various autoimmune diseases, tests were conducted on blood samples from patients with systemic lupus erythematosus. This group (n=40) had 10% ASA reactivity. Patients suffering from chronic fatigue syndrome have a set of symptoms similar to GWS, but only 15% (n—30) showed reactivity to ASA. Prior studies have shown that the majority of individuals who develop atypical connective tissue disease after receiving SBI have serum antibodies reactive to a synthetic polymer (Tenenbaum S. A., et al. *Lancet.* 349: 449–454, 1997). Both silicone and acrylamide, like squalene, are potent immunological adjuvants. Therefore, we tested for cross-reactive antibodies to squalene in serum from patients exposed to SBI which had signs and symptoms of atypical connective tissue disease. Only 10% of this group (n=30) were reactive to squalene.

Example 11
Determining ASA Levels in Individuals Previously Exposed to Squalene.

In the course of these studies two subjects who had volunteered to participate in a vaccine trial at the NIH involving the use of squalene as an adjuvant were examined. Subsequent to participating in our study, they developed a multisystemic disease process similar to that seen in Persian Gulf veterans. One received a single injection and became ill within a few weeks, with signs and symptoms including arthropathy, myalgia, lymphadenopathy, rashes, fatigue, headaches, and fasciculations. The patient has lower than normal levels of acetylcholinesterase, and histological evidence for lymphocytic infiltrates around vascular tissue and IgG mediated demyelinization. This patient had the NIH vaccine study code broken and found only the adjuvant squalene had been administered as a placebo. This patient was only weakly positive for ASA. Another patient who went through the whole experimental immunization protocol before manifesting a similar set of symptoms scored a 3+for reactivity to ASA.

All of the methods and compositions disclosed and claimed herein can be made and executed without undue experimentation in light of the present disclosure. While the methods and compositions of this invention have been described in terms of preferred embodiments, it will be apparent to those of skill in the art that variations may be applied to the methods and compositions, as well as the steps or in the sequence of steps of the methods described herein without departing from the concept, spirit and scope of the invention. All such similar substitutes and modifications apparent to those skilled in the art are deemed to be within the spirit, scope and concept of the invention.

What is claimed is:

1. A method for detecting antisqualene antibody comprising the steps of:

providing a test sample suspected of containing an antisqualene antibody;

contacting the test sample and squalene, wherein the squalene complexes with the antisqualene antibody to form a binary complex;

contacting the binary complex with an indicator reagent, wherein the indicator reagent complexes with the binary complex to form a ternary complex; and detecting the presence or absence of the ternary complex.

2. The method of claim 1, wherein the test sample is obtained from a bodily fluid.

3. The method of claim 1, wherein the test sample is obtained from blood.

4. The method of claim 1, wherein the squalene is immobilized on a solid support.

5. The method of claim 4, wherein the solid support is a membrane, plastic, agarose bead, or magnetic bead.

6. The method of claim 4, wherein the solid support is polypropylene, polystyrene, polyvinylchloride, polyamide, polycarbonate, polyether, polymethyl methacrylate, nitrocellulose, polyvinylidene difluoride, agarose, metal, or nylon.

7. The method of claim 4, wherein the solid support is a nitrocellulose membrane.

8. The method of claim 1, wherein the indicator reagent is conjugated to a detectable label.

9. The method of claim 8, wherein the detectable label is a protein, enzyme, radioisotope, nucleic acid segment, fluorochrome, or fluorescent protein.

10. The method of claim 9, wherein the enzyme is horseradish peroxidase, alkaline phosphatase, or β-galactosidase.

11. The method of claim 9, wherein the enzyme catalyzes the conversion of a non-chemiluminescent reagent into a chemiluminescent product.

12. The method of claim 9, wherein the enzyme catalyzes the conversion of a non-colorimetric reagent to a colorimetric product.

\* \* \* \* \*